United States Patent
Lin

(10) Patent No.: US 6,590,135 B1
(45) Date of Patent: Jul. 8, 2003

(54) SANITARY NAPKIN HAVING FAR-INFRARED EFFECTS

(76) Inventor: Pao-Yu Lin, 5F, No. 2 Lane 121, Pei Hsin Road, Section 2, Hsintien City, Taipei Hsien (TW)

( * ) Notice: Subject to any disclaimer, the term of this patent is extended or adjusted under 35 U.S.C. 154(b) by 0 days.

(21) Appl. No.: 09/583,235

(22) Filed: May 31, 2000

(51) Int. Cl.[7] ................................................ A61F 13/15
(52) U.S. Cl. ........................ 604/362; 604/387; 604/904
(58) Field of Search ................................. 604/360, 362, 604/367, 375, 386, 387, 904, 6.08; 210/748; 250/432 R; 607/100, 154

(56) References Cited

U.S. PATENT DOCUMENTS

| | | | | |
|---|---|---|---|---|
| 5,192,277 A | * | 3/1993 | Chung et al. | 604/360 |
| 5,785,698 A | * | 7/1998 | Van Iten | 604/387 |
| 5,814,078 A | * | 9/1998 | Zhou et al. | 607/1 |
| 6,026,330 A | * | 2/2000 | Chuang | 607/100 |
| 6,108,581 A | * | 8/2000 | Jung | 607/100 |
| 6,186,992 B1 | * | 2/2001 | Roe et al. | 604/385.01 |
| 6,395,955 B1 | * | 5/2002 | Roe et al. | 604/361 |

FOREIGN PATENT DOCUMENTS

| | | | | |
|---|---|---|---|---|
| EP | 0 489 538 | * | 6/1992 | A61N/5/06 |
| JP | 02-57252 A | * | 8/1988 | 604/359 |
| JP | 63-304037 A | * | 12/1988 | C08J/9/04 |
| JP | 02-154071 A | * | 6/1990 | D06M/15/00 |
| JP | 02-174861 A | * | 7/1990 | A61N/5/06 |
| JP | 03-097904 A | * | 4/1991 | A41D/31/02 |
| JP | 03-136670 A | * | 6/1991 | A61N/5/06 |
| JP | 03-191957 A | * | 8/1991 | A61F/13/02 |

* cited by examiner

*Primary Examiner*—Weilun Lo
*Assistant Examiner*—Michael Bogart
(74) *Attorney, Agent, or Firm*—Dennison, Schultz & Dougherty

(57) ABSTRACT

A sanitary napkin having a far-infrared functional component disposed between a lower bottom layer and a middle water-absorbent layer of the sanitary napkin is provided. The far-infrared functional component emits far-infrared rays that have direct far-infrared effects on a user's skin contacting with an upper surface layer of the sanitary napkin as well as on the user's lower belly close to the sanitary napkin. The sanitary napkin has therefore an additional value of being physiologically beneficial to users.

4 Claims, 7 Drawing Sheets

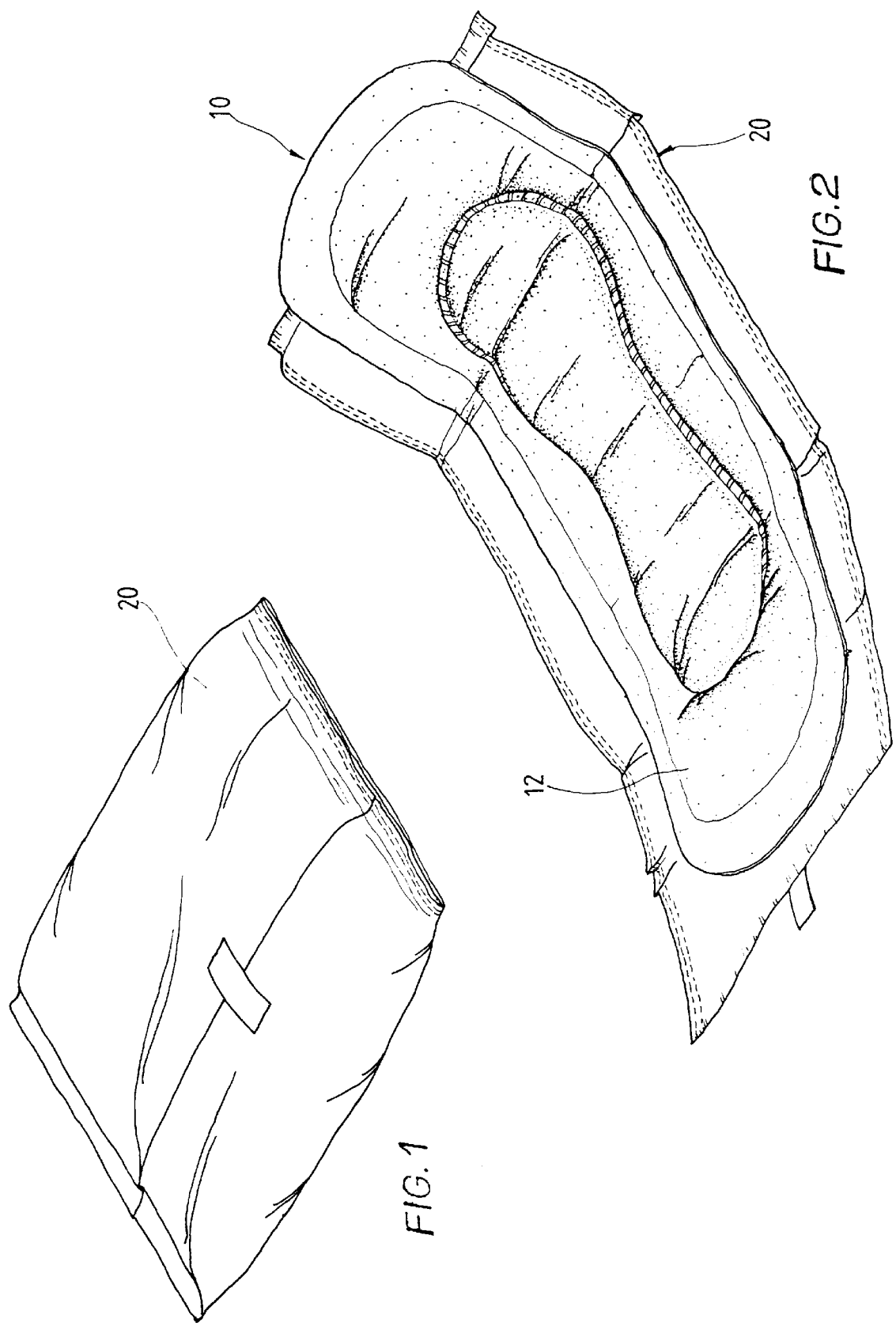

SANITARY NAPKIN HAVING FAR-INFRARED EFFECTS

BACKGROUND OF THE INVENTION

The present invention relates to a sanitary napkin, and more particularly to a sanitary napkin having a far-infrared functional component provided therein to beneficially affect a user's physiological condition through far-infrared effects produced by the far-infrared functional component.

It is known that far-infrared rays are a kind of electromagnetic waves having wavelength within the range from 4 to 400 micrometers. The far-infrared rays are characterized by the inherent radioactivity, penetrating ability, and ability of resonant absorption. It has been medically proven that far-infrared rays within a certain wavelength range are capable of producing heat effect as a result of the action of resonant absorption between a far-infrared material and a human body, and this heat effect causes a raised temperature at an area deep under the skin, expanded capillaries and enhanced circulation to remove obstacles, such as bruise, in the metabolism, revitalize body organization, and stimulate the formation of enzymes. All of these medical effects on the human body by the far-infrared rays indicate that the far-infrared rays indeed have positive influences on improved metabolism and are therefore physiologically beneficial to the human body.

There are also many studies proving that ceramic material is a radioactive body that need not have any particular heat source but the human body temperature to provide the same far-infrared effect. As a result, the ceramic material has been known as a non-expensive and good far-infrared functional component. The radioactive ceramic material in the form of superfine powder is most preferable for use and can be doped with various kinds of metal oxide depending on actual need. The ceramic material and every other added materials are heated to a temperature about 1600° C. to produce the above-mentioned superfine powder. Such superfine powder of ceramic material can be effectively transferred onto articles made of other materials by different ways. For example, when the superfine powder of ceramic material is mixed with a painting material, the resultant mixture is a far-infrared functional component that may be printed or coated on the surface of general articles, such as different types of cloth, and then the cloth can be processed to make, for example, bed sheet, underwear, socks, etc. Or, the resultant mixture may be added into other materials for making other products, such as insulating cushion, flooring, etc. Since all the previously illustrated articles and/or products containing ceramic material are frequently used in our daily life to contact with our skin, the far-infrared functional component thereof would have good far-infrared effects on our body to improve our physiological conditions.

A sanitary napkin is a product having close relation with most women. Conventionally, the sanitary napkin has only one basic function of absorbing body fluids. Most efforts made to improve the sanitary napkin are focused on its structural design in order to make it more air-permeable and comfortable in contact with a user's skin without giving too much help in improving the user's physiological conditions. It would therefore be beneficial to women if the sanitary napkin were provided with a far-infrared functional component to move beyond its original and only function of absorbing body fluid and to effectively reduce some uncomfortable conditions, such as bellyache and waist sores accompanying with menses.

SUMMARY OF THE INVENTION

It is therefore a primary object of the present invention to provide a sanitary napkin having far-infrared effects. The sanitary napkin of the present invention includes a far-infrared functional component disposed in the sanitary napkin at a suitable position, preferably a position between a middle water-absorbent layer and a lower water-impermeable bottom layer of the sanitary napkin, so that the far-infrared functional component has direct and helpful far-infrared effects on the user's skin and lower belly that contacting with and close to the sanitary napkin, respectively, and therefore makes the sanitary napkin physiologically useful to the user.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein FIG. 1 is a perspective of an individually packed conventional sanitary napkin;

FIG. 2 is a perspective of the conventional sanitary napkin of FIG. 1 in an unpacked and stretched form;

DETAILED DESCRIPTION OF THE PREFERRED EMBODIMENTS

Figure 3:
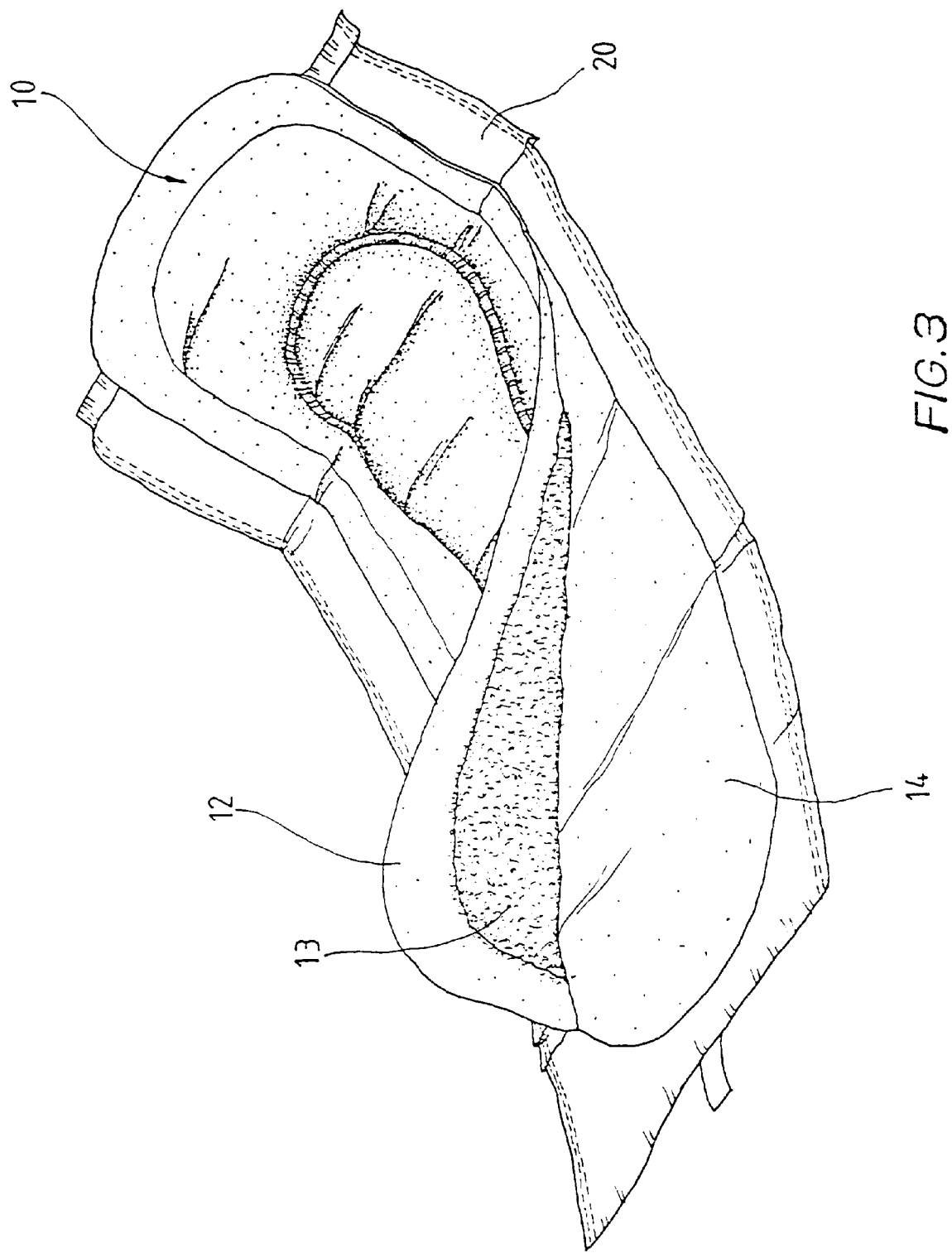
FIG. 3 is a perspective of the conventional sanitary napkin of FIG. 2 with a surface layer thereof being partially separated from a bottom layer thereof to show an internal structure of the sanitary napkin.

Please refer to FIGS. 1, 2 and 3 in which a conventional sanitary napkin 10 is shown. The sanitary napkin 10 is usually folded and individually packed in a bag 20 made of a waterproof plastic material 20, as shown in FIG. 1, and includes an upper surface layer 12 that has an outer side for contacting with a user's skin, a lower bottom layer 14 that has a outer surface for contacting with a user's underwear and is usually made of a thin water-impermeable material to prevent any body fluid from permeating through the bottom layer 14 to smear the underwear, and a middle water-absorbent layer 13 of suitable thickness sealed between the surface and the bottom layers 12 and 14, as can be best seen in FIG. 3. A layer of suitable adhesive 11, that is not shown in FIGS. 1 through 3 but may be found in FIG. 4 as a reference, is applied on the outer side of the bottom layer 14.

With the adhesive layer 11, the sanitary napkin 10 may be detachably adhered to an inner side of a packing material of suitable size. The sanitary napkin 10 and the packing material are then together folded in a predetermined manner and the folded packing material is sealed in a predetermined manner to form the bag 20, as shown in FIG. 1, in which the sanitary napkin 10 is received. To use the sanitary napkin 10, the bag 20 is opened and the sanitary napkin 10 is removed from the packing material 20. Thereafter, the sanitary napkin 10 can be adhered to the user's underwear with the same adhesive layer 11 applied on the outer side of the bottom layer 13.

Figure 4:
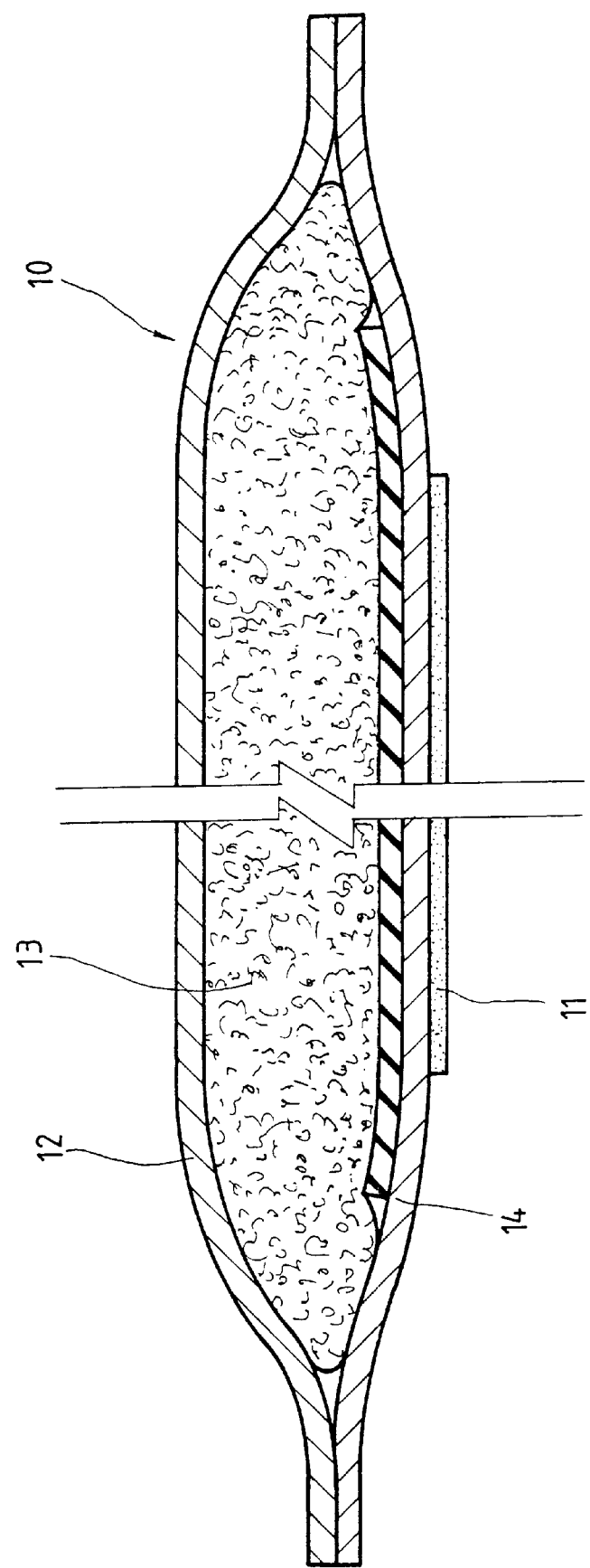
FIG. 4 is an enlarged sectional view of a sanitary napkin according to the present invention.
Figure 5:
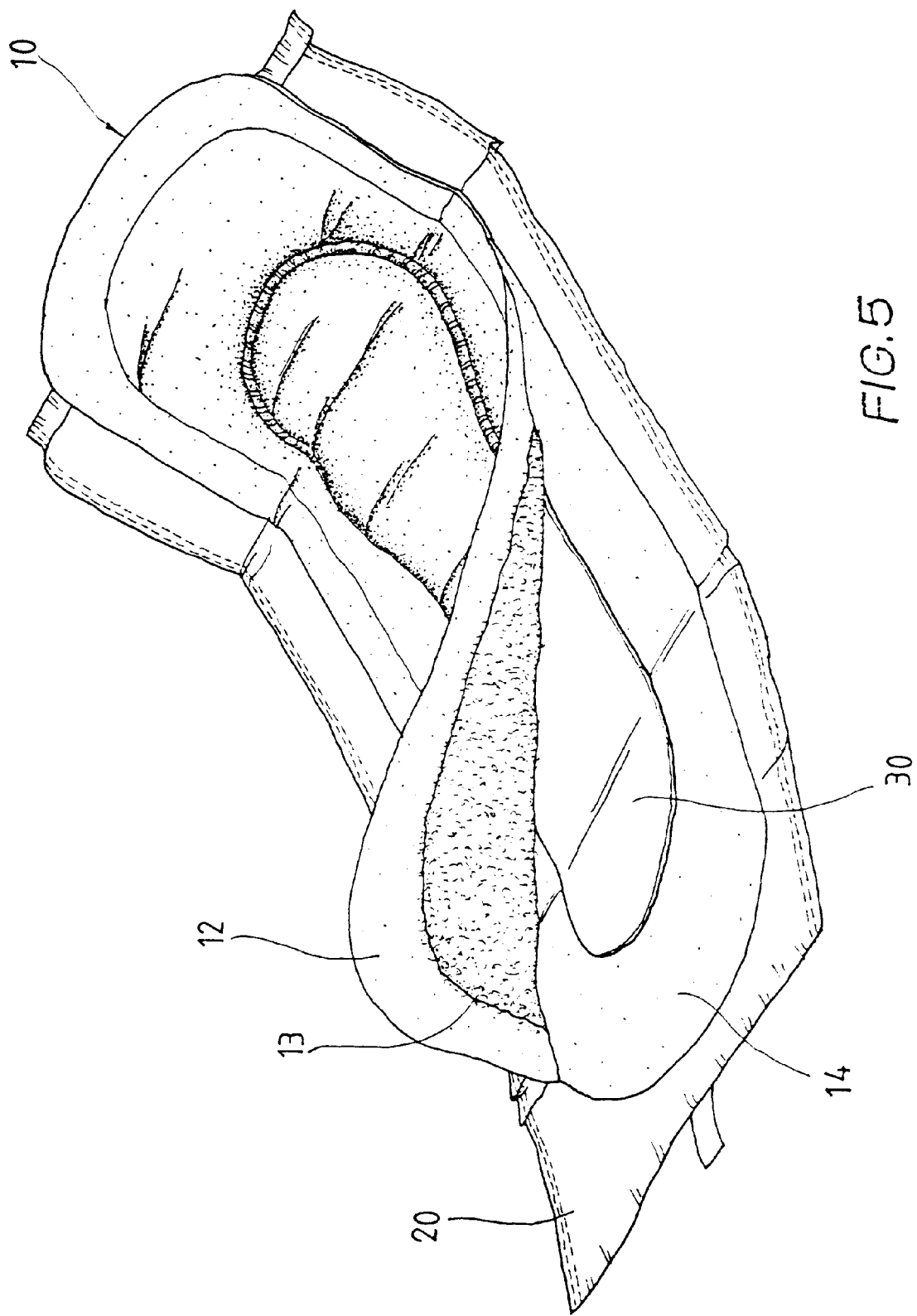
FIG. 5 is a perspective of a sanitary napkin according to a first embodiment of the present invention, wherein the surface layer thereof is partially lifted to show an internal structure thereof.

Please now refer to FIGS. 4 and 5 that are sectional and perspective views, respectively, of a sanitary napkin 10 provided between the water-absorbent layer 13 and the bottom layer 14 with a far-infrared functional component 30 that is capable of providing some proven far-infrared effects. The far-infrared functional component 30 is prepared from adequate amount of ceramic powder and other specific materials, so that the far-infrared functional component 30 is substantially in the form of a thin sheet with suitable width and length. The thin sheet of far-infrared functional component 30 is preferably laid between the water-absorbent layer 13 and the bottom layer 14 when forming the sanitary napkin 10. The positioning of the far-infrared functional component 30 preferably between the water-absorbent layer 13 and the bottom layer 14 so that the far-infrared functional component 30 is located directly below the water-absorbent layer 13 relative to the user's skin would avoid any possible isolation of far-infrared rays emitted by the far-infrared functional component 30 from effectively reaching the user's skin due to the bottom layer 14 that is usually made of water-impermeable plastic material. To have the far-infrared functional component 30 located in the above-mentioned position, it is usually to directly attach the far-infrared functional component 30 to an inner side of the bottom layer 14. A far-infrared functional component 30 additionally laid in the sanitary napkin 10 at this position would not affect any originally intended function of the sanitary napkin 10 but produces direct and healthy far-infrared effects on the user's skin contacting with the sanitary napkin 10 and other areas, such as lower belly, making the sanitary napkin 10 of the present invention a physiologically beneficial product.

Figure 6:
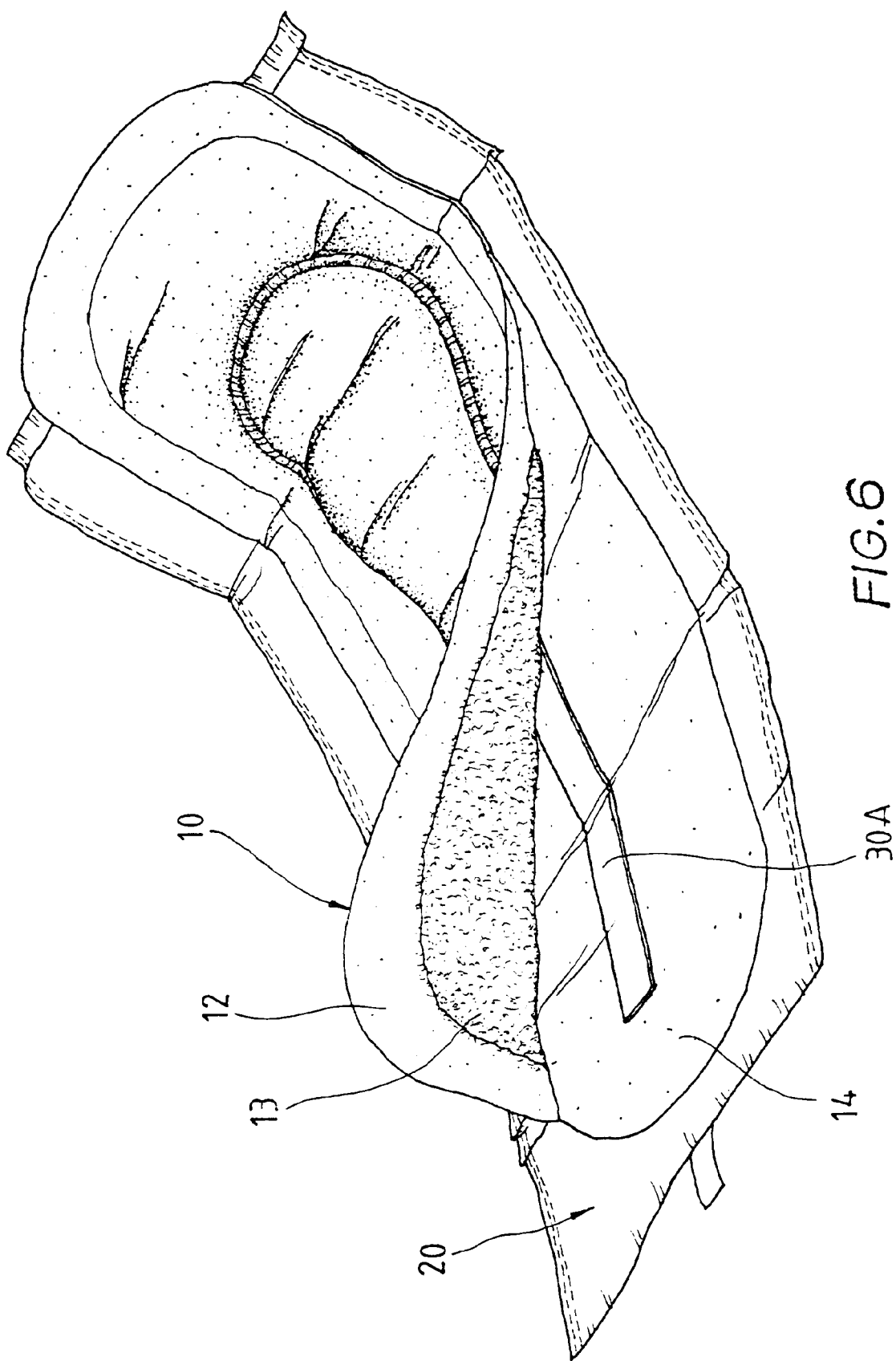
FIG. 6 is a perspective of a sanitary napkin according to a second embodiment of the present invention, wherein the surface layer thereof is partially lifted to show an internal structure thereof.
Figure 7:
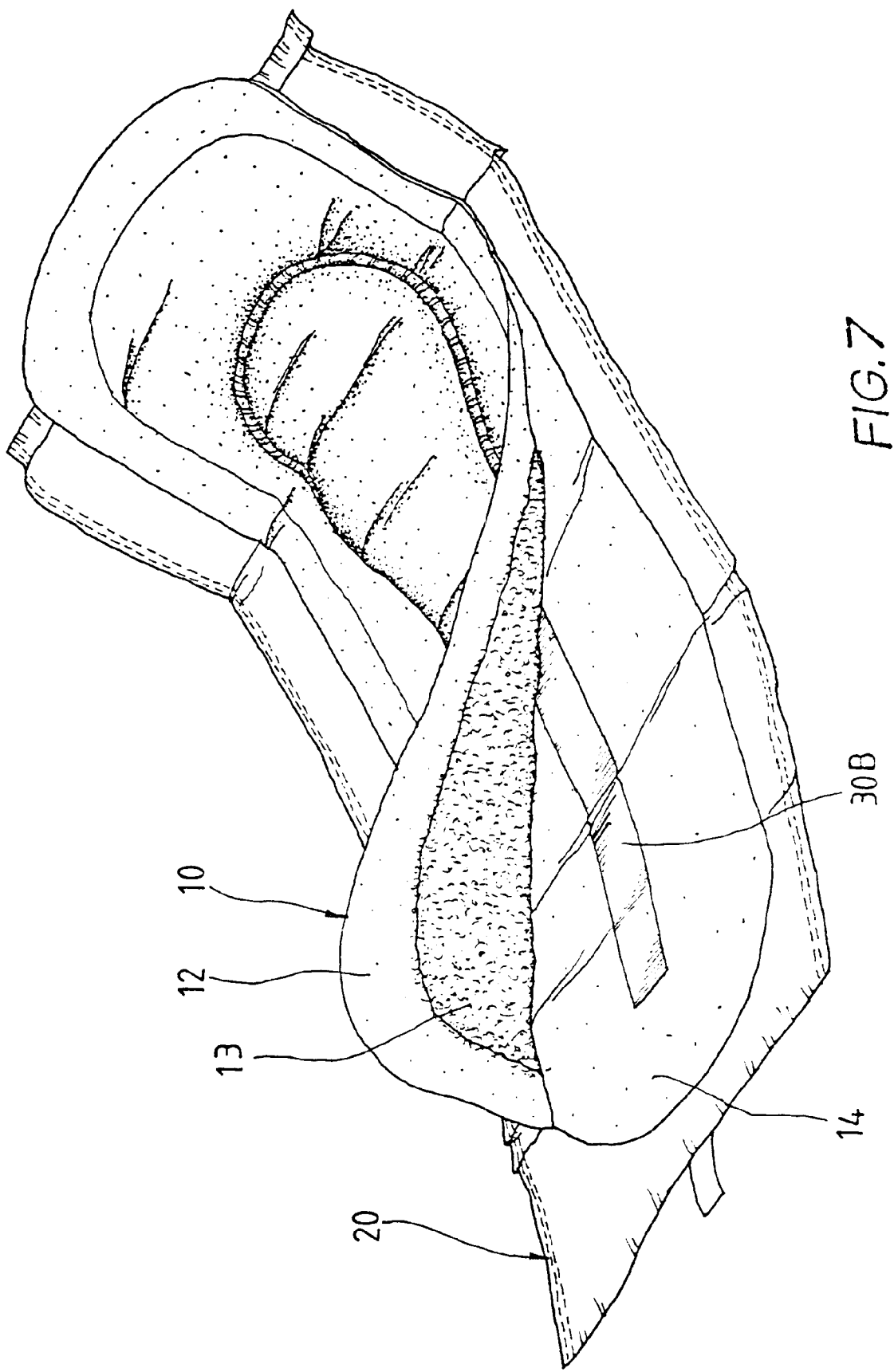
FIG. 7 is a perspective of a sanitary napkin according to a third embodiment of the present invention, wherein the surface layer thereof is partially lifted to show an internal structure thereof.
Figure 8:
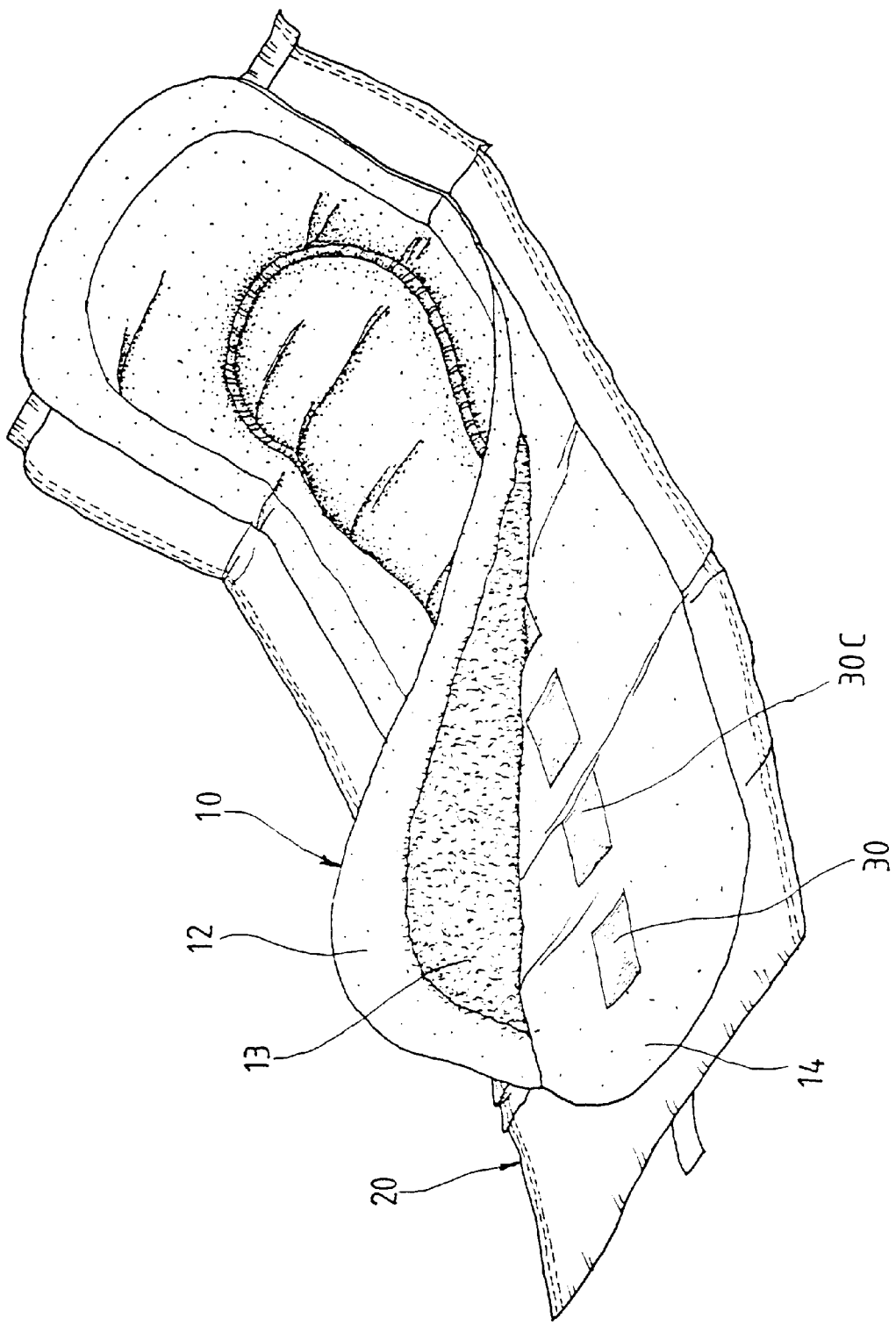
FIG. 8 is a perspective of a sanitary napkin according to a fourth embodiment of the present invention, wherein the surface layer thereof is partially lifted to show an internal structure thereof.

Since the far-infrared functional component 30 is not limited to any shape, size, and manner in which it is laid on the inner side of the bottom layer 14, it is possible to provide the sanitary napkin 10 of the present invention with different degree of intensity of far-infrared effects depending on actual needs simply by changing the shape, size or number of the far-infrared functional component 30 in the sanitary napkin 10. In a first embodiment of the present invention as shown in FIG. 5, there is provided the far-infrared functional component 30 that is a one single wide and long piece additionally attached to the bottom layer 14. In a second embodiment of the present invention as shown in FIG. 6, there is provided a far-infrared functional component 30A that is a one single narrow and long strip additionally attached to the bottom layer 14. In a third embodiment of the present invention as shown in FIG. 7, there is provided a far-infrared functional component 30B that is a one single narrow and long strip directly printed onto the inner side of the bottom layer 14. And, in a fourth embodiment of the present invention as shown in FIG. 8, there is provided a plurality of far-infrared functional components 30C that are directly printed onto the inner side of the bottom layer 14 at equal space. The above-mentioned differently shaped, sized and located far-infrared functional components 30, 30A, 30B, and 30C may be selectively employed depending on the cost of the far-infrared materials and/or the manufacturing process of the sanitary napkin 10. It is, of course, most preferable to select one or more of the illustrated and many other possible types of the far-infrared functional components that would be most favorable to enable mass production of the sanitary napkin 10, so that the sanitary napkin of the present invention can be supplied to effectively help women in their physiological condition without increasing too much of its selling price.

What is claimed is:

1. A sanitary napkin having far-infrared effects comprising a sanitary napkin including a far-infrared functional component disposed in said sanitary napkin at a predetermined position, said far-infrared functional component being so positioned in said sanitary napkin that far-infrared rays emitted by said far-infrared functional component produce direct effects on a user's skin contacting with said sanitary napkin, wherein said sanitary napkin includes an upper surface layer for contacting with a user's skin, a middle water-absorbent layer, and a lower bottom layer made of water-impermeable plastic sheet, said lower bottom layer including an inner surface adjacent to said middle water-absorbent layer, and said far-infrared functional component being disposed on said inner surface of said lower bottom layer between said middle water-absorbent layer and said lower bottom layer to avoid possible isolation of said far-infrared rays emitted by said far-infrared functional component from the user's skin due to said plastic sheet of said lower bottom layer.

2. A sanitary napkin having far-infrared effects as claimed in claim 1, wherein said far-infrared functional component includes a wide and long strip attached to an inner surface of said lower bottom layer.

3. A sanitary napkin having far-infrared effects as claimed in claim 1, wherein said far-infrared functional component includes a narrow and long strip directly printed onto said inner surface of said lower bottom layer.

4. A sanitary napkin having far-infrared effects as claimed in claim 2, wherein said far-infrared functional component includes a plurality of spaced segments directly printed onto said inner surface of said lower bottom layer.

* * * * *